(12) United States Patent
Malm et al.

(10) Patent No.: US 7,144,909 B2
(45) Date of Patent: Dec. 5, 2006

(54) PHENOXY SUBSTITUTED BENZOCONDENSED HETEROARYL DERIVATIVES AS THYROID RECEPTOR LIGANDS

(75) Inventors: Johan Malm, Trångsund (SE); Erik Flöistrup, Sundbyberg (SE); Spiros Grivas, Enskede (SE); Yi-Lin Li, Huddinge (SE)

(73) Assignee: Karo Bio AB, Huddinge (SE)

( * ) Notice: Subject to any disclaimer, the term of this patent is extended or adjusted under 35 U.S.C. 154(b) by 530 days.

(21) Appl. No.: 10/470,878

(22) PCT Filed: Jan. 30, 2002

(86) PCT No.: PCT/EP02/00957

§ 371 (c)(1),
(2), (4) Date: Jan. 12, 2004

(87) PCT Pub. No.: WO02/062780

PCT Pub. Date: Aug. 15, 2002

(65) Prior Publication Data

US 2004/0116387 A1    Jun. 17, 2004

(30) Foreign Application Priority Data

Feb. 8, 2001  (GB) .................... 0103175.6
Mar. 2, 2001  (GB) .................... 0105234.9

(51) Int. Cl.
*A61K 31/4184* (2006.01)
*C07D 235/04* (2006.01)

(52) U.S. Cl. ............. 514/399; 548/300.1; 548/302.7; 548/304.4; 548/310.1; 549/429; 549/497; 514/396; 514/465

(58) Field of Classification Search ............ 548/300.1, 548/302.7, 304.4, 310.1; 549/429, 497; 514/396, 514/399, 465
See application file for complete search history.

(56) References Cited

U.S. PATENT DOCUMENTS

| | | | | |
|---|---|---|---|---|
| 5,637,593 A | * | 6/1997 | Porter et al. ............ | 514/274 |
| 6,380,213 B1 | * | 4/2002 | Panetta et al. ........... | 514/312 |
| 6,472,387 B1 | * | 10/2002 | Panetta et al. .......... | 514/227.8 |
| 6,794,406 B1 | | 9/2004 | Haning et al. | |

FOREIGN PATENT DOCUMENTS

| | | |
|---|---|---|
| WO | WO 99/00353 | 1/1999 |
| WO | WO 00/39077 | 7/2000 |
| WO | WO 01/70687 A1 | 9/2001 |
| WO | WO 02/051805 A1 | 7/2002 |

OTHER PUBLICATIONS

Naokata Yokoyama, et al.: Journal of Medicinal Chemistry, vol. 38, No. 4, pp. 695-707 (1995).
Charles M. Buess, et al.: Department of Chemistry, University of Southern California, pp. 469-474 (1965).

* cited by examiner

*Primary Examiner*—Golam M. M. Shameem
(74) *Attorney, Agent, or Firm*—Todd E. Garabedian; Wiggin and Dana LLP

(57) ABSTRACT

This invention relates to novel compounds which are thyroid receptor ligands, preferably antagonists, and to methods for using such compounds in the treatment of cardiac and metabolic disorders, such as cardiac arrhythmias, thyrotoxicosis, subcllinical hyperthyrodism and liver diseases.

14 Claims, No Drawings

PHENOXY SUBSTITUTED BENZOCONDENSED HETEROARYL DERIVATIVES AS THYROID RECEPTOR LIGANDS

FIELD OF THE INVENTION

This invention relates to novel compounds which are thyroid receptor ligands, preferably antagonists, and to methods for using such compounds in the treatment of cardiac and metabolic disorders, such as cardiac arrhythmias, thyrotoxicosis, subclinical hyperthyrodism and liver diseases.

BACKGROUND OF THE INVENTION

Nuclear hormone receptors comprise a class of intracellular, mostly ligand-regulated transcription factors, which include receptors for thyroid hormones. Thyroid hormones exert profound effects on growth, development and homeostasis in mammals. They regulate important genes in intestinal, skeletal and cardiac muscles, liver and the central nervous system, and influence the overall metabolic rate, cholesterol and triglyceride levels, heart rate, and affect mood and overall sense of well being.

There are two major subtypes of the thyroid hormone receptor, TRα and TRβ, expressed from two different genes. Differential RNA processing results in the formation of at least two isoforms from each gene. The $TR\alpha_1$, $TR\beta_1$ and $TR\beta_2$ isoforms bind thyroid hormone and act as ligand-regulated transcription factors. The $TR\alpha_2$ isoform is prevalent in the pituitary and other parts of the central nervous system, does not bind thyroid hormones, and acts in many contexts as a transcriptional repressor. In adults, the $TR\beta_1$ isoform is the most prevalent form in most tissues, especially in the liver and muscle. The $TR\alpha_1$ isoform is also widely distributed, although its levels are generally lower than those of the $TR\beta_1$ isoform. A growing body of data suggest that many or most effects of thyroid hormones on the heart, and in particular on the heart rate and rhythm, are mediated through the $TR\alpha_1$ isoform, whereas most actions of the hormones on the liver, muscle and other tissues are mediated more through the β-forms of the receptor. It is believed that the α-isoform of the receptor is the major drive to heart rate for the following reasons: (i) tachycardia is very common in the syndrome of generalized resistance to thyroid hormone in which there are defective TRβ-isoforms, and consequently high circulating levels of $T_4$ and $T_3$; (ii) Tachycardia was observed in the only described patient with a double deletion of the TRβ gene (Takeda et al, J. Clin. Endrocrinol. & Metab. 1992, Vol. 74, p. 49); (iii) a double knockout TRα gene (but not β-gene) in mice showed bradycardia and lengthening of action potential compared to control mice (Forrest, D.; Vennström, B. Functions of Thyroid Hormone Receptors in Mice. *Thyroid*, 2000, 10, 41–52); (iv) western blot analysis of human myocardial TRs show presence of the $TR\alpha_1$, $TR\alpha_2$ and $TR\beta_2$ proteins, but not $TR\beta_1$. If the indications above are correct, an α-selective thyroid hormone receptor antagonist that interacts selectively with the heart would offer an attractive alternative treatment of heart related disorders, such as atrial and ventricular arrhythmias.

Atrial fibrillation (AF) is the most common type of sustained arrhythmia encountered in primary care practice and is significantly more common in elderly patients, thus reflecting a reduction in the threshold for AF with age. Pharmacological treatment of AF involves the following types of anti-arrhythmic drugs according to Vaughan-Williams classification: (i) of class I such as disopyramide and flecainide (sodium channel blocker); (ii) of class IV such as amiodarone (potassium channel blocker, prolongation of repolarization); (iii) of class IV such as verapamil and dilitazem (calcium channel blocker). Many patients are also subjected to electric cardioversions in order to convert atrial fibrillation into sinus rhythm. It should be noted that current therapies are associated with pro-arrhythmic risks and anti-arrhythmic agents often have insufficient efficacy partly because effective doses are limited by side-effects.

Ventricular arrhythmia, especially sustained ventricular tachycardia (VT) and ventricular fibrillation (VF) is the main cause of death associated with heart attack. Historically, three types of antiarrhythmic agents, class I agents, β-adrenergic blockers (class II), amiodarone and sotalol, appeared to offer the best scope for mortality reduction in patients with cardiac disease by preventing the occurrence of VT/VF.

The outcome of CAST (Cardiac Arrhythmia Supression Trial, N. Engl. J. Med., 321 (1989) 406–412) and its successor SWORD (Survival With Oral D-sotatol trial, 1994) created much concern regarding the potential of class I agents and sotalol. It was found that class I agents did not decrease mortalities in patient groups at risk for sudden cardiac death. For some subsets of patients, class I agents even proved to increase mortality. The SWORD trial was stopped when sotalol proved to give higher death rate in patients, compared with the placebo. A consequence of these results is that the use of implantable defibrillators and surgical ablation have increased and that the trend in the industry has been towards the development of highly specific class III agents. Some of these channel blockers have been withdrawn from clinical development due to proarrhythmic effects and the subject remains under intensive debate. In this context it should be noted that amiodarone, despite its complex pharmacokinetics, mode of action (amiodarone is not regarded as a pure class III agent) and numerous side effects, is currently considered by many to be the most effective agent in the control of both atrial and ventricular arrhythmia.

Thyrotoxicosis is the clinical syndrome that results when tissues are exposed to elevated levels of circulating thyroid hormones, thyroxine (3,5,3',5'-tetraiodo-L-thyronine, or $T_4$) and triiodothyronine (3,5,3'-triiodo-L-thyronine, or $T_3$). Clinically, this state often manifest itself in weight loss, hypermetabolism, lowering of serum LDL levels, cardiac arrhythmias, heart failure, muscle weakness, bone loss in postmenopausal women, and anxiety. In most instances, thyrotoxicosis is due to hyperthyroidism, a term reserved for disorders characterized by overproduction of thyroid hormones by the thyroid gland. The ideal treatment of hyperthyroidism would be the elimination of its cause. This is however not possible in the more common diseases producing thyroid hypersecretion. At present, treatment of hyperthyroidism is directed to reduce overproduction of thyroid hormones by inhibiting their synthesis or release, or by ablating thyroid tissue with surgery or radioiodine. Drugs inhibiting thyroid hormone synthesis, release or peripheral conversion of $T_4$ to $T_3$ include antithyroid drugs (thionamides), iodide, iodinated contrast agents, potassium perchlorate and glucocorticoids. The main action of antithyroid drugs such as methimazole (MMI), carbimazole, and propylthiouracil (PTU), is to inhibit the organification of iodide and coupling of iodotyrosines, thus blocking the synthesis of thyroid hormones. As they neither inhibit iodide transport nor block the release of stored thyroid hormones, control of hyperthyroidism is not immediate and in most cases requires 2 to 6 weeks. Factors that determine the speed of restoration of euthyroidism include disease activity, initial levels of circulating thyroid hormones, and intrathyroidal hormone stores. Serious side effects are not common with antithyroid drugs. Agranulocytosis is the the most feared problem and have been observed with both MMI or PTU treatment. Elderly people may be more susceptible to this side effect, but agranulocytosis can occur in any age group, although less frequently in younger people. Inorganic iodide given in pharmacological doses (as Lugol's solution or as a saturated solution of potassium iodide, SSKI) decreases its own transport into the thyroid, thus inhibiting iodide organification (the Wolff-Chaikoff effect), and rapidly blocks the release of $T_4$ and $T_3$ from the gland. However, after a few days or weeks, its antithyroid action is lost, and thyrotoxicosis recurs or may worsen. Short-term iodide therapy is used to prepare patients for surgery, usually in combination with a thionamide drug. Iodide is also used in the management of severe thyrotoxicosis (thyroid storm), because of its ability to inhibit thyroid hormone release acutely. Perchlorate interferes with accumulation of iodide by the thyroid. Gastric irritation and toxic reactions limit the long-term use of perchlorate in the management of hyperthyroidism. Glucocorticoids in high doses inhibit the peripheral conversion of $T_4$ to $T_3$. In Graves' hyperthyroidism, glucocorticoids appear to decrease $T_4$ secretion by the thyroid, but the efficiency and duration of this effect is unknown. The aim of surgical treatment or radioiodine therapy of hyperthyroidism is to reduce the excessive secretion of thyroid hormones by removal or destruction of thyroid tissue. Subtotal or near-total thyroidectomy is performed in Graves' disease and toxic multinodular goiter. Restoration of euthyroidism before surgery is mandatory. The classical approach combines a course of thionamide treatment to restore and maintain euthyroidism, and the preoperative administration of iodide for approximately 10 days in order to induce involution of the gland. Propranolol and other beta-adrenergic antagonist drugs are useful in controlling tachycardia and other symptoms of sympathetic activation.

A high affinity ThR antagonist would in principle have the ability to restore euthyrodism quicker than any of the above agents, considering that its action is competitive for the ThR receptor. Such an agent could be used either alone or in combination with the above drugs, or alternatively before an ablative treatment. It may also serve as a safer substitute for antithyroid drugs, especially in elderly patients at a high risk of agranulocytosis. Furthermore, hyperthyrodism can aggravate pre-existing heart disease and also lead to atrial fibrillation (AF), congestive heart failure, or worsening of angina pectoris. In the elderly patient, often with mild but prolonged elevation of plasma thyroid hormones, symptoms and signs of heart failure and complicating AF may dominate the clinical picture and mask the more classical endocrine manifestations of the disease.

DESCRIPTION OF THE INVENTION

In accordance with the present invention, compounds are provided which are thyroid receptor ligands, and have the general formula

I:

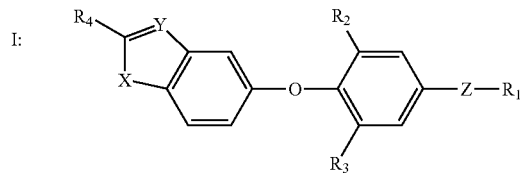

or pharmaceutically acceptable salts, stereoisomers, prodrug ester forms or radioactive forms thereof, wherein;

$R_1$ is selected from: carboxylic acid (—$CO_2H$), phosphonic acid (—$PO(OH)_2$), phosphamic acid (—$PO(OH)NH_2$), sulphonic acid (—$SO_2OH$), and hydroxamic acid (—CONHOH) groups;

Z is selected from: —$(CH_2)_n$—, and —$(CH_2)_m$—CH($R^a$)—;

$R_2$ and $R_3$ are independently selected from: halogen, $C_{1-4}$ alkyl, and $C_{1-4}$alkyl substituted with 1, 2 or 3 $R^b$ groups which may be the same or different;

$R_4$ is selected from: $C_{6-10}$ aryl, $C_{5-9}$ heteroaryl, $C_{1-4}$ alkyl, and $C_{1-4}$ alkyl substituted with 1, 2, or 3 $R^c$ groups which may be the same or different, said aryl and heteroaryl being optionally substituted with 1, 2, or 3 $R^d$ groups which may be the same or different;

X is selected from: —O—, —S—, and —N($R^e$)—;

Y is selected from: —CH—, and —N—;

$R^a$ is selected from: —OH, —$NH_2$, —NH($C_{1-4}$alkyl), —NH($C_{2-4}$alkenyl), and —NH($C_{2-4}$alkynyl), or a bioisosteric equivalent;

$R^b$ is selected from: hydrogen, fluorine, or a bioisosteric equivalent;

$R^c$ is selected from: hydrogen, $C_{6-10}$ aryl, $C_{5-9}$ heteroaryl, $C_{6-10}$ aryloxy, $C_{5-9}$ heteroaryloxy, N($C_{6-10}$ aryl)$_2$, —NH($C_{6-10}$ aryl), —N($C_{5-9}$ heteroaryl)$_2$, —NH($C_{6-9}$ heteroaryl), —N($C_{1-4}$ alkyl)($C_{6-10}$ aryl), —N($C_{1-4}$ alkyl)($C_{6-9}$ heteroaryl), and —N($C_{6-10}$ aryl)($C_{5-9}$ heteroaryl) or a bioisosteric equivalent;

$R^d$ is selected from: hydrogen, fluorine, —OH, $C_{1-2}$ alkoxy, N($C_{1-4}$ alkyl)$_2$, and —NH($C_{1-4}$ alkyl) or a bioisosteric equivalent;

$R^e$ is selected from: hydrogen, and $C_{1-2}$ alkyl;

n is 1, 2 or 3;

m 1 or 2;

DETAILED DESCRIPTION OF THE INVENTION

The following definitions apply to the terms as used throughout this specification, unless otherwise limited in specific instances.

The term "thyroid receptor ligand" as used herein covers any chemical substance which can bind to a thyroid receptor. The ligand may act as an antagonist, an agonist, a partial antagonist or a partial agonist.

The term "alkyl" as employed herein alone or as part of another group means an acyclic straight or branched-chain radical, containing 1 to 4 carbons, as exemplified by methyl, propyl, iso-propyl, sec-butyl. Alkyl also includes a radical where 1 to 3 hydrogens attached to carbon have been replaced by fluorine. When $R_2$ and $R_3$ are selected from alkyl and substituted by fluorine, the preferred radical is —$CF_3$.

The term "alkenyl" as used herein by itself or as part of another group means a straight or branched-chain radical with 2 to 4 carbon atoms and one carbon to carbon double bond, as exemplified by a normal chain radical such as ethenyl, propenyl and butenyl. As described above with respect to "alkyl" the straight or branched portion of the alkenyl group may be optionally substituted when a substituted alkenyl group is provided.

The term "alkynyl" as used herein by itself or as part of another group means a straight or branched-chain radical of 2 to 4 carbons and one carbon to carbon triple bond, as exemplified by a normal chain radical such as ethenyl, propenyl and butenyl. As described above with respect to the "alkyl" the straight or branched portion of the alkynyl group may be optionally substituted when a substituted alkynyl group is provided.

The term "aryl" as employed herein alone or as part of another group means a monocyclic or bicyclic aromatic group, consisting of 6, 7, 8, 9 or 10 carbon atoms in the ring portion, including partially saturated rings such as indanyl and tetrahydronaphthyl. The preferred aryl groups are phenyl, which may be substituted with 1 to 3 groups selected from $R^d$ which groups may be the same or different.

The term "halogen" means fluorine, chlorine, bromine and iodine.

The term "oxo" as used herein as a part of another group, exemplified by "alkoxy", "aryloxy" and "heteroaryloxy", refers to a carbon-oxygen-carbon bond system where the carbon part can be alkyl, aryl or heteroaryl as herein defined. One example is the term "alkoxy" which refers to those groups of the designated carbon length in either a straight or branched configuration attached through an oxygen linkage and if two or more carbons in length, they may incude one double or a triple bond. Examples of such alkoxy groups are methoxy, ethoxy, propoxy, allyloxy, propargyloxy, butoxy, isobutoxy, tertiary butoxy, and the like. Alkoxy also refer to a radical where 1 to 3 hydrogens can be replaced by fluorine at the available carbons. When $R_2$ is selected from alkoxy and substituted by fluorine, the preferred group radicals is —$OCF_3$.

The term "heteroaryl" as used herein alone or as a part of another group refers to a group containing 5 to 9 carbon atoms, where the aromatic ring includes 1 to 4 heteroatoms, such as nitrogen, oxygen or sulfur. Such rings may be fused to another aryl or heteroaryl ring, and include possible N-oxides. The heteroaryl group may optionally be substituted at the available carbons with 1 to 3 substituents of $R^d$ which may be the same or different.

When $R_1$ and $R^c$ is selected from heterocycles it refers mainly to 6 membered rings.

The term "phosphonic acid" and "phosphamic acid" refers to a phosphorus-containing group of the structures:

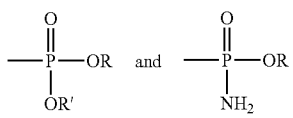

wherein R and R' are independently selected from hydrogen and $C_{1-4}$ alkyl.

The term "bioisosteric equivalent" refers to compounds or groups that possess near equal molecular shapes and volumes, approximately the same distribution of electrons, and which exhibit similar physical and biological properties. Examples of such equivalents are: (i) fluorine vs. hydrogen, (ii) oxo vs. thia, (iii) hydroxyl vs. amide, (iv) carbonyl vs. oxime, (v) carboxylate vs. tetrazole. Examples of such bioisosteric replacements can be found in the literature and examples of such are: (i) Burger A, *Relation of chemical structure and biological activity*; in Medicinal Chemistry Third ed., Burger A, ed.; Wiley-Interscience: New York, 1970, 64–80; (ii) Burger, A.; "Isosterism and bioisosterism in drug design"; *Prog. Drug Res.* 1991, 37, 287–371; (iii) Burger A, "Isosterism and bioanalogy in drug design", *Med Chem. Res.* 1994, 4, 89–92; (iv) Clark R D, Ferguson A M, Cramer R D, "Bioisosterism and molecular diversity", *Perspect. Drug Discovery Des.* 1998, Sep. 10, 1911, 213–224; (v) Koyanagi T, Haga T, "Bioisosterism in agrochemicals", *ACS Symp. Ser.* 1995, 584, 15–24; (vi) Kubinyi H, "Molecular similarities. Part 1. Chemical structure and biological activity", *Pharm. Unserer Zeit* 1998, 27, 92–106; (vii) Lipinski C A.; "Bioisosterism in drug design"; *Annu. Rep. Med Chem.* 1986, 21, 283–91; (viii) Patani G A, LaVoie E J, "Bioisosterism: A rational approach in drug design", *Chem. Rev. (Washington, D.C.)* 1996, 96, 3147–3176; (ix) Soskic V, Joksimovic J, "Bioisosteric approach in the design of new dopaminergic/serotonergic ligands", *Curr. Med Chem.* 1998, 5, 493–512 (x) Thomber C W, "Isosterism and molecular modification in drug design", *Chem. Soc. Rev.* 1979, 8, 563–80.

The compounds of formula I can be present as salts, in particular "pharmaceutically acceptable salts". A compound having at least one acid group (for example —COOH) can form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri lower alkylamine, for example ethyl, tertbutyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds I or their pharmaceutically acceptable salts, are also included. Preferred salts of the compounds of formula I which include an acid group include sodium, potassium and magnesium salts and pharmaceutically acceptable organic amines.

The compounds of formula I having at least one basic center (for example —$NEt_2$) can also form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$–$C_4$) alkyl or arylsulfonic acids which are unsubstituted or substituted, for example by halogen, for example methyl- or p-toluenesulfonic acid. Corresponding acid addition salts can also be formed having, if desired, an additionally present basic center. Salts which are unsuitable for pharmaceutical uses but which can be employed, for example, for the isolation or purification of free compounds I or their pharmaceutically acceptable salts, are also included. Preferred salts of the compounds of formula I which include a basic groups include monohydrochloride, hydrogensulfate, methanesulfonate, phosphate or nitrate.

An acid center (for example when $R_1$ is —COOH) part in formula I can form "prodrug ester forms" known in the art such as pivaloyloxymethyl or dioxolenylmethyl. Such prodrug esters are described in standard references such as Chapter 31, written by Camille G. Wermuth et al., in "The Practice of Medicinal Chemistry", ed. C. G. Wermuth, Academic Press, 1996 (and the references contained therein).

Certain compounds of the invention can be "stereoisomers", which have one or more asymmetric centers and can exist in the form of racemates, single enantiomers, as individual diastereomers, with all possible isomers, and mixtures thereof, all of which are within the scope of the invention.

$R_1$ may preferably be a carboxylic acid group (—$CO_2H$).

$R_2$ and $R_3$ may preferably be independently selected from bromine or chlorine, in which case $R_1$ is preferably a carboxylic acid group (—$CO_2H$).

In certain preferred compounds of formula I n is 1 or 2 and $R^a$ is —OH or —$NH_2$, in which case $R_1$ is preferably a carboxylic acid group (—$CO_2H$), and $R_2$ and $R_3$ are preferably independently selected from bromine and chlorine.

In certain preferred compounds of the present invention in formula I $R^c$ and $R^d$ are hydrogen, in which case $R_1$ is preferably a carboxylic acid group (—$CO_2H$), $R_2$ and $R_3$ is preferably bromine or chlorine, n is preferably 1 or 2, m is preferably 1, and $R_1$ is preferably —OH or —$NH_2$.

In some preferred compounds according to formula I X is —O—, and Y is —CH—, in which case $R_1$ is preferably a carboxylic acid group (—$CO_2H$), $R_2$ and $R_3$ are preferably bromine, n is preferably 1 or 2, m is preferably 1, $R^a$ is preferably —OH or —$NH_2$, and $R_c$ and $R^d$ are preferably hydrogen.

In some preferred compounds formula I X is —$N(R^e)$— and Y is —N— or —CH—, in which case $R_1$ is preferably a carboxylic acid group (—$CO_2H$), $R_2$ and $R_3$ are preferably independently selected from bromine and chlorine, n is preferably 1 or 2, m is preferably 1, $R^a$ is preferably —OH or —$NH_2$, and $R^c$ and $R^d$ are preferably hydrogen.

In some preferred compounds formula I is —$(CH_2)_n$—, $R_2$ and $R_3$ are independently selected from chlorine and bromine; $R_4$ is $C_{1-4}$ alkyl; X is —$N(R^e)$—; Y is —N—; $R^c$ is hydrogen; $R^e$ is hydrogen or $C_{1-2}$ alkyl; and n is 1, in which case $R_1$ is preferably a carboxylic acid group (—$CO_2H$).

In some preferred compounds formula I $R_2$ and $R_3$ are bromine; X is —O—; Y is —CH—; $R^a$ is —OH or H; $R^c$ is $C_{6-10}$ aryl or $C_{6-10}$ aryloxy; $R^d$ is hydrogen or $C_{1-4}$ alkyl; n is 1 or 2; and m is 1, in which case $R_1$ is preferably a carboxylic acid group (—$CO_2H$), $R_4$ is preferably $C_{6-10}$ aryl or $C_{5-9}$ heteroaryl; Z is preferably —$(CH_2)_n$—; and $R^d$ is preferably hydrogen.

Compounds of the invention include, but are not limited to, the following:
- 3,5-Dibromo-4-(2-phenyl-5-benzofuranyloxy)phenylacetic acid;
- 3,5-Dibromo-4-(5-benzimidazolyloxy)phenylacetic acid;
- 3,5-Dibromo-4-(1-N-methyl-5-benzoimidazolyloxy)phenylacetic acid;
- 3,5-Dibromo-4-(2-methyl-5-benzimidazolyloxy)phenylacetic acid;
- 3,5-Dichloro-4-(2-isopropyl-5-benzimidazolyloxy)phenylacetic acid;
- 3-[3,5-Dibromo-4-(2-(3-tolyl)-5-benzofuranyloxy)phenyl]propionic acid and pharmaceutically acceptable salts thereof, and stereoisomers thereof.

The compounds of formula I may be prepared by the processes described by way of example in the following reaction schemes. Examples of reagents and procedures for these reactions appear hereinafter and in the worked Examples.

Compounds of formula I of the invention can be prepared using the method indicated in Scheme 1 below. In Scheme 1, a biaryl ether 1 is regioselectively iodinated in the ring portion to give 2. A mixture of iodine and a silver salt can be used in the present procedure with success, but further combinations of iodinating agents may be employed and are well known to those skilled in the art. Some examples of such alternative procedures can involve: (i) chloramine T and sodium iodide in DMF, DMSO, or acetonitrile. T. Kometani, D. S. Watt, T. 3, Tetrahedron Lett., 1985, 26, 2043; (ii) a reagent prepared in situ from sodium hypochlorite and sodium iodide. K. J. Edgar, S. N. Falling, J. Org. Chem., 1990, 55, 5287. (iii) reaction of aromatic compounds with copper salts and an iodide donor. W. C. Baird and J. H. Surrage, J. Org. Chem., 1970, 10, 3436. (iv) Iodine react with aromatic substrates in the presence of dehydated aluminia at room temperature. R. M. Pagni et al., J. Org. Chem., 1988, 53, 4477; (v) benzylammonium dichloroiodate in acetic acid in the presence of $ZnCl_2$ at room temperature or at 70° C. S. Kajigaeshi et al., Bull. Soc. Chem. Jpn. 1989, 62, 1349. (vi) oxidative monoiodination in the presence of equimolar amounts of alkali-metal iodides. D. I. Makhon'kov, A. V. Cheprakov and I. P. Beletskaya, J. Chem. Rev., 1989, 2029. Furthermore, it should be realized that the ring portion also can be substituted with iodide after the methyl ether has been hydrolysed.

The iodine compound 2 is cross-coupled with an substituted acetylene, employing suitable palladium-catalysis conditions well known to those skilled in the art and well reviewed in the literature. A suitable organic base such as triethylamine, diethylamine or diisopropylamine is used to form the benzofuran ring in situ. After standard work-up, the ester function is removed by treatment with 3–6 molar equivalents of a base such as sodium hydroxide at room temperature, dissolved in a solvent such as methanol.

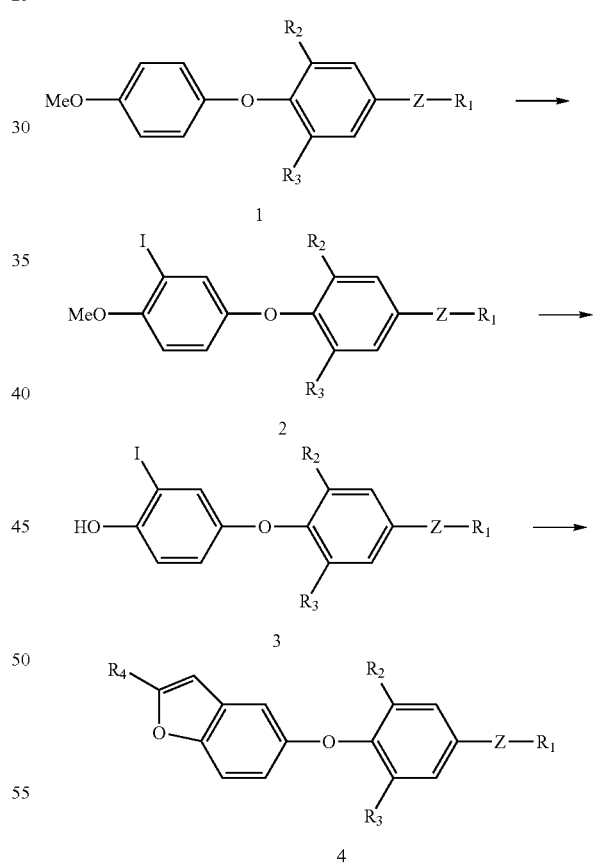

Scheme 1

Example 1: $R_1$ = COOH; $R_2$,$R_3$ = Br; $R_4$ = Ph; Z = $(CH_2)_n$; n = 1.
Example 6: $R_1$ = COOH; $R_2$,$R_3$ = Br; $R_4$ = m-tol; Z = $(CH_2)_n$; n = 2.

Example 1: $R_1$=COOH; $R_2$,$R_3$=Br; $R_4$=Ph; Z=$(CH_2)_n$; n=1.

Example 6: $R_1$=COOH; $R_2$,$R_3$=Br; $R_4$=m-tol; Z=$(CH_2)_n$; n=2.

The compounds of the invention are antagonists or partial antagonists. As such they are useful in medical therapy.

Furthermore, they are useful in the prevention, inhibition or treatment of a disease which is dependent on the expression of a $T_3$ regulated gene or associated with metabolic dysfunction. Examples of such diseases are heart related disorders, such as cardiac arrhythmias (atrial and ventricular arrhythmias), especially atrial fibrillation and ventricular tachycardia and fibrillation. The compounds of the invention may also be useful in the treatment of thyrotoxicosis, especially in the therapy of elderly patients, subclinical hyperthyroidism, and other related endocrine disorders related to thyroid hormone.

Compounds of the invention may also be T3 antagonists with a preferential hepatic activity, and such may be used in medical treatment to improve the clinical course of various liver diseases such as: alcoholic liver disease, viral liver diseases (Hepatis A, B, C, D, E) and immnunological liver diseases. The T3-antagonist may have principal activity in the liver with minimal activity in the rest of the body and thus reduce side-effects associated with the treatment. It is known that induction of a state with abnormally low levels of circulating thyroid hormones (hypothyroidism) is a rewarding treatment of liver diseases such as hepatic cirrhosis/fibrosis. Nevertheless, induction of hypothyroidism it is not an accepted therapy for liver diseases. The major reason is that currently-available methods to induce hypothyroidism inevitably lead to a general hypothyroid state since the production of $T_4$ in the thyroid is blocked. General, systemic hypothyroidism causes a number of unacceptable clinical symptoms such as myxedema, depression, constipation etc. Also, the time of onset from initiation of therapy until hypothyroidism is manifest is rather long, typically several months. T3-receptor antagonists also induce hypothyroidism but much faster than standard therapies. A T3-receptor antagonist with major accumulation in the liver spares the body from the deleterious impact of general hypothyroidism. The compounds of the invention may therefore be used to treat certain liver diseases, such as chronic alcoholism, acute hepatitis, chronic hepatitis, hepatitis C-induced liver cirrhosis, and liver fibrosis.

The compounds of the invention may also be used to treat certain skin disorders or diseases such as keloids, roughened skin, lichen planus, ichtyosis, acne, psoriasis, Dernier's disease, eczema, chloracne, atopic dermatitis, pityriasis, hirsuitism and skin scarring. In treating skin disorders or diseases as described above, the compounds of the invention may be used in combination with a retinoid or a vitamin D analog.

Exemplifying the invention is a pharmaceutical composition comprising any of the compounds described above, including combinations of them, and a pharmaceutically acceptable carrier. Also included is a process for making a pharmaceutical composition comprising combining any of the compounds described above and a pharmaceutically acceptable carrier.

Another embodiment of the invention is a method of treating, inhibiting or preventing a disease which is dependent on the expression of a $T_3$ regulated gene or associated with metabolic dysfunction by administering to a mammal in need thereof a therapeutically effective amount of any of the compounds or pharmaceutical compositions described above. The said diseases may be heart related disorders, such as cardiac arrhythmias (atrial and ventricular arrhythmias), especially atrial fibrillation and ventricular tachycardia and fibrillation, especially in the therapy of elderly patients, subclinical hyperthyroidism, and other endocrine disorders related to thyroid hormone.

Yet another embodiment of the invention is a method of treating, inhibiting or preventing certain skin disorders or diseases such as keloids, roughened skin, lichen planus, ichtyosis, acne, psoriasis, Dernier's disease, eczema, chloracne, atopic dermatitis, pityriasis, hirsuitism and skin scarring. In treating skin disorders or diseases as described above, the compounds of the invention may be used in combination with a retinoid or a vitamin D analog.

Further exemplifying the invention is the use of any of the compounds described above in the preparation of a medicament for the treatment, inhibition or prevention of a disease which is dependent on the expression of a $T_3$ regulated gene or associated with metabolic dysfunction. Still further exemplifying the invention is the use of any of the compounds desribed above in the preparation of a medicament for the treatment and/or prevention of heart related disorders, such as cardiac arrhytrmias (atrial and ventricular arrhythmias), especially atrial fibrillation and ventricular tachycardia and fibrillation, especially in the therapy of elderly patients, subclinical hyperthyroidism, and other endocrine disorders, related to thyroid hormone.

Further exemplifying the invention is the use of any of the compounds described above in the preparation of a medicament for the treatment, inhibition or prevention of certain skin disorders or diseases such as keloids, roughened skin, lichen planus, ichtyosis, acne, psoriasis, Dernier's disease, eczema, chloracne, atopic dermatitis, pityriasis, hirsuitism and skin scarring. In treating skin disorders or diseases as described above, the compounds of the invention may be used in combination with a retinoid or a vitamin D analog.

The compounds of the present invention can be administered in such oral dosage forms as tablets, capsules (each of which includes sustained release or timed release formulations), pills, powder, granules, elixirs, tinctures, suspensions, syrups and emulsions. Likewise, they may also be administered in intravenous (bolus or infusion), intraperitoneal, topical (e.g., ocular eyedrop), subcutaneous, intramuscular, or transdermal (e.g., patch) forms, all using techniques well known to those of ordinary skill in the pharmaceutical arts.

The dosage regimen for the compounds of the present invention will be selected in accordance with a variety of factors including the type, species, age, weight, sex, and medical condition of the patient; the severity of the condition to be treated; the route of administration; the renal and hepatic function of the patient; and the particular compound or salt thereof employed. An ordinarily-skilled physician, veterinarian or clinician can readily determine and prescribe the effective amount of the drug required to prevent, counter or arrest the progress of the condition.

Oral dosages of the present invention, when used for the indicated effects, will preferably range between about 0.01 mg per kg of body weight per day (mg/kg/day) to about 100 mg/kg/day, more preferably 0.01 mg per kg of body weight per day (mg/kg/day) to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100, and 500 milligrams of the active ingredient for the symptomatic adjustment of the dosage to the patient to be treated. A medicament typically contains from about 0.01 mg to about 500 mg of the active ingredient, preferably from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in staged doses two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms includes sodium oleate, sodium stearate, magnesium stearate, sodium benzoate, sodium acetate, sodium chloride and the like. Disintegrators include without limitation starch, methylcellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed form a variety of phospholipids, such as cholesterol, stearylamine or phosphatidylcholines.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example in "Design of Prodrugs" ed. H. Bundgaard, Elsevier, 1985, which is incorporated by reference herein in its entirety. Metabolites of the compounds includes active species produced upon introduction of compounds of this invention into the biological milieu.

EXAMPLES

The following Examples represent preferred embodiments of the present invention. However, they should not be construed as limiting the invention in any way.

Example 1

3,5-Dibromo-4-(2-phenyl-5-benzofuranyloxy)phenylacetic Acid (a) To a suspension of bis(4-methoxyphenyl)iodonium tetrafluoroborate (prepared analogously to the method of Yokayama et al, Journal of Medicinal Chemistry 1995, 38, 695–707) (31 g, 0.072 mmol) and copper bronze (6.1 g, 0.096 mmol) in dichloromethane (150 mL), was added a solution of methyl [3,5-dibromo-4-hydroxyphenyl]acetate (15.6 g, 0.048 mmol) and triethylamine (5.4 g, 0.053 mmol) in dichloromethane (100 mL) dropwise at room temperature. The mixture was stirred overnight and then filtrated through Celite. After concentration, the resulting residue was passed through a short silica gel column eluted with ethyl acetate/light petroleum ether (5/95). The pure fractions were pooled and concentrated to dryness. The residue was recrystallized from methanol affording 15.5 g (75%) of methyl [3,5-dibromo-4-(4-methoxyphenoxy)phenyl]acetate.

(b) Methyl[3,5-dibromo-4-(4-methoxyphenoxy)phenyl]acetate (1.0 g, 2.3 mmol), silver (I) sulfate (1.6 g, 4.6 mmol) and methanol (10 mL) was stirred in the dark at −78° C. Iodide (1.2 g, 4.6 mmol) was added and the reaction mixture was allowed to reach room temperature after 10 minutes. The yellow precipitate was filtered off, the eluate dissolved in ethyl actetate and washed with water. After concentration of the organic phase, 0.82 g (64%) of methyl [3,5-dibromo-4-(4-methoxy-3-iodophenoxy)phenyl]acetate was obtained.

(c) Methyl[3,5-dibromo-4-(4-methoxy-3-iodophenoxy)phenyl]acetate (0.82 g, 1.5 mmol) was dissolved in dichloromethane (25 mL) and cooled down to −78° C. Boron tribromide (8.8 mL, 1 N in dichloromethane) was added and the reaction mixture was stirred at −20° C. for 30 hours. Water was added to the reaction mixture, the organic phase separated and concentrated. The residue was filtered on a short column (silica, dichloromethane/ethyl acetate 1:1), to give 0.73 g (90%) of methyl [3,5-dibromo-4-(4-hydroxy-3-iodophenoxy)-phenyl]acetate as a beige solid mass.

(d) Methyl[3,5-dibromo-4-(4-hydroxy-3-iodophenoxy)phenyl]acetate (730 mg, 1.3 mmol), phenylacetylen (210 mg, 2.1 mmol) and bis(triphenylphosphine)palladium (II) chloride (82 mg, 0.12 mmol), copper (I) iodide (32 mg, 0.17 mmol) and triethylamine (11 mL) was stirred at reflux. After 2 hours, dichloromethane (2 mL) was added to the reaction mixture, followed by further heating for 16 hours. The reaction mixture was allowed to cool down to room temperature, dissolved in dichloromethane and washed once with a saturated solution of aqueous ammonium chloride. The organic phase was dried over sodium sulphate and concentrated. The residue was purified on column (silica gel, gradient elution from chloroform/heptane 1:2, to chloroform/methanol 5:1), to give 600 mg (86%) of methyl[3,5-dibromo-4-(2-phenyl-5-benzofuranyloxy)phenyl]acetate as a pale yellow solid mass. $^1$H-NMR (300 MHz, DMSO-d$_6$): δ 7.87 (d, J=7.4 Hz, 2H), 7.76 (s, 2H), 7.61 (d, J=9.2 Hz, 1H), 7.53 (t, 3H), 7.42 (d, J=7.1 Hz, 1H), 7.35 (s, 1H), 6.90 (s, 1H), 3.82 (s, 2H), 3.67 (s, 3H).

(e) Methyl[3,5-dibromo-4-(2-phenyl-5-benzofuranyloxy)phenyl]acetate (200 mg) was diluted in ethanol (2 mL) and treated with an aqueous saturated solution of potassium hydroxide (0.5 mL). The reaction mixture was refluxed for 1.5 hours. The reaction mixture was concentrated, diluted with chloroform and washed with an aqueous solution of hydrochloric acid (1 N). The organic phase was dried over magnesium sulphate, filtered and concentrated. This gave 0.13 g (70%) of 3,5-dibromo-4-(2-phenyl-5-benzofuranyloxy)-phenylacetic acid as a beige solid mass. $^1$H-NMR (300 MHz, DMSO-d$_6$): δ 12.5 (br s, 1H), 7.86 (d, J=7.2 Hz, 2H), 7.34 (s, 2H), 7.61 (d, J=8.4 Hz, 1H), 7.50 (t, J=5.1 Hz, 3H), 7.42 (d, J=7.1, 1H), 7.35 (s, 1H), 6.87 (s, 1H), 3.70 (s, 2H).

Example 2

3,5-Dibromo-4-(5-benzimidazolyloxy)phenylacetic Acid (a) Methyl[3,5-dibromo-4-(4-methoxyphenoxy)phenyl] acetate (8 g, Example 1(a)) was dissolved in acetic acid (80 mL) and potassium nitrate (2.4 g) was added. The reaction mixture was cooled down to −10° C. and nitric acid (40 mL) was added dropwise during one minute, while keeping the internal temperature below 4° C. The cooling bath was removed and after three hours at room temperature the reaction mixture was poured out on ice. The formed yellow precipitate was filtered off and washed with water. The precipitate was taken up in chloroform and washed with water. The organic phase was dried over magnesium sulphate, filtered and concentrated. This gave 8.1 g (92%) of methyl [3,5-dibromo-4-(4-methoxy-3-nitrophenoxy)phenyl] acetate.

(b) To methyl [3,5-dibromo-4-(4-methoxy-3-nitrophenoxy)phenyl]acetate (5 g), dissolved in 2-(2-methoxyethoxy)ethanol (50 mL) was added an aqueous solution of ammonia (32%, 7 mL). The reaction mixture was heated at 150° C. for, with continuos refill of ammonia. After 24 hours, water was added followed by an aqueous solution of hydrochloric acid. This was continued until the acidity of the solution reached pH 2. The aqueous phase was extracted with chloroform, washed with brine and dried over magnesium sulphate. After concentration of the organic phase, 4.1 g (84%) of methyl [3,5-dibromo-4-(4-amino-3-nitrophenoxy)phenyl]acetate was obtained as an yellow solid mass.

(c) Methyl[3,5-dibromo-4-(4-amino-3-nitrophenoxy)phenyl]acetate (1 g) was dissolved in methanol (10 mL) and hot solution of sodium dithionite (6.1 g) in water (30 mL) was added. The reaction mixture was refluxed for 26 hours, ethanol (255 mL) was added and the formed precipitate filtered off through a pad of celite. The filtrate was concentrated to a constant volyme of 20 mL to which formic acid (16 mL) was added. After reflux for 4 hours, the reaction mixture was cooled down to room temperature, the formed yellow precipitate filtered off and washed with methanol. Recrystallisation from ethanol gave 0.4 g (42%) of 3,5-dibromo-4-(5-benzimidazolyloxy)phenylacetic acid. $^1$H-NMR (300 MHz, DMSO-d$_6$): δ 12.55 (br s, 1H), 9.47 (s, 1H), 8.27 (s, 1H), 7.88 (d, J=3.0 Hz, 1H), 7.70 (s, 2H), 6.97 (d, J=9 Hz, 1H), 6.34 (dd, J=8.9 Hz, J=3.1 Hz, 1H), 3.68 (s, 2H).

Example 3

3,5-Dibromo-4(1-N-methyl-5-benzoimidazolyloxy) phenylacetic Acid (a) Methylamine (40 mL) was added to a solution of methyl [3,5-dibromo-4-(4-ethoxy-3-nitrophenoxy)phenyl] acetate (3.5 g, Example 2(b)) in methoxyethoxyethanol (80 mL). After two hours at reflux the reaction mixture was cooled down and diluted with chloroform. The organic phase was washed with brine, dried over magnesium sulphate and concentrated. This gave 4.2 g (95%) of methyl [3,5-dibromo-4-(4-methylamino-3-nitro-phenoxy)phenyl] acetate as an orange solid mass.

(b) Methyl[3,5-dibromo-4-(4-methylamino-3-nitrophenoxy)phenyl]acetate (4.1 g) was dissolved in methanol (10 mL) and a hot solution of sodium dithionite (6.1 g) in water (30 mL) was added. After reflux for two hours, hot methanol was poured into the reaction mixture. The formed precipitate was filtered off and the filtrate concentrated. The residue was dissolved in formic acid and refluxed. After two hours, water (2 mL) was added to the reaction mixture followed by an aqueous solution of hydrochloric acid (35%, 2 mL) one hour later. After 6.5 hours a beige precipitate was filtered off and washed with methanol. This gave 0.2 g (20%) of 3,5-dibromo-4-(1-methyl-5-benzoimidazolyloxy)phenylacetic acid.

(c) The reaction mixture was refluxed for 26 hours, ethanol (255 mL) was added and the formed precipitate filtered off through a pad of celite. The filtrate was concentrated to a constant volyme of 20 mL to which formic acid (16 mL) was added. After reflux for 4 hours, the reaction mixture was cooled down to room temperature, the formed yellow precipitate filtered off and washed with methanol. Recrystallisation from ethanol gave 0.4 g (42%) of 3,5-dibromo-4-(1-N-methyl-5-benzimidazolyloxy)phenylacetic acid. $^1$H-NMR (300 MHz, DMSO-d$_6$) δ 12.57 (s, 1H), 8.16 (s, 1H), 7.75 (s, 1H), 7.54 (d, J=8.8 Hz, 1H), 6.90 (dd, J=8.8 Hz, 1H), 6.77 (d, J=2.3 Hz, 1H), 3.82 (s, 3H), 3.71 (s, 2H).

Example 4

3,5-Dibromo-4-(2-methyl-5-benzimidazolyloxy) phenylacetic Acid (a) Methyl[3,5-dibromo-4-(4-amino-3-nitrophenoxy)phenyl]acetate (1.1 g, Example 2(b)) was treated with sodium dithionite as described in Example 2(c). The formed methyl [3,5-dibromo-4-(3,4-diaminophenoxy)phenyl]acetate was dissolved in methanol (36 mL). An aqueous solution of hydrochloric acid (35%, 2.1 mL) was added, followed by acetylacetone (0.48 g). The reaction mixture was refluxed for 5.5 hours, cooled down and the formed yellow precipitate was filtered off. After recrystallisation from ethanol, 80 mg (5%) of methyl [3,5-dibromo-4-(2-methyl-5-benzoimidazolyloxy)phenyl]acetate was obtained.

(b) Methyl[3,5-dibromo-4-(2-methyl-5-benzoimidazolyloxy)phenyl]acetate (41 mg) was hydrolysed using the method as described in Example 1(e). This gave 21 mg (52%) of 3,5-dibromo-4-(2-methyl-5-benzoimidazolyloxy) phenylacetic acid as a brown crystal mass. $^1$H-NMR (300 MHz, MeOD-d$_4$): δ 7.60 (s, 2H), 6.70 (d, J=8.8 Hz, 1H), 6.29 (d, J=2.9 Hz, 1H), 6.01 (dd, J=3.0 Hz, J=8.7 Hz, 1H), 2.94 (s, 3H), 2.70 (s, 2H).

Example 5

3,5-Dichloro-4-(2-isopropyl-5-benzimidazolyloxy) phenylacetic Acid (a) A mechanically stirred solution of 2,6-dichlorophenol (100 g) in acetonitrile (400 mL) was cooled to 0° C. and bromine (108 g) in acetonitrile (100 mL) was added dropwise. The red solution was stirred at 0° C. for an additional two hours and an saturated aqueous solution of sodium sulphite was added until the red color disappeared. The phases were separated and the aqueous phase was extracted three times with ethyl acetate. Concentration of the combined organic phases gave 4-bromo-2,6-dichlorophenol as a yellow oil, which crystallized on standing. The crystalline material was washed with water and dried to give 126 g (85%) of colorless crystals.

(b) A mechanically stirred solution of 4-bromo-2,6-dichlorophenol (110 g), 4-fluoro-nitrobenzene (64 g), potassium carbonate (84 g) and copper powder (3.3 g) in dimethylform-amide (400 ml) was heated at 135° C. for 45 hours. The reaction was cooled to room temperature and concentrated. The residue was dissolved in ethyl acetate and washed twice with sodium hydroxide (2 N), twice with hydrochloric acid (1.2 N) and brine. After concentration of the organic phase, the residue was recrystallized (acetone/water, 4:1) to give 79 g (45%/o) of a three to one mixture of 3,5-dichloro-4-(4-nitrophenoxy)bromobenzene and 3,5-dichloro-4-(4-nitrophenoxy)benzene as yellow crystals.

(c) To the products above (40 g), dichlorobis(triphenylphosphine)palladium (II) (0.39 g) and copper(I) iodide (0.21 g) was added triethylamine (17 g) in acetonitrile (75 mL), followed by trimetylsilylacetylene (16 g) in acetonitrile (25 mL). The reaction mixture was stirred under an atmosphere of nitrogen at 60° C. for one hour and then cooled to room temperature. The reaction mixture was concentrated and the residue dissolved in ethyl acetate. The organic phase was washed twice with water and once with brine. After concentration of the organic phase, the residue was purified on column (n-heptane/ethyl acetate, 8:1) to give 42 g (53%) of 3,5-dichloro-4-(4-nitrophenoxy)trimetylsilylacetylenebenzene as yellow crystals.

(d) Cyclohexene (39 g, 0.48 mol) was added dropwise to a solution of borane (240 mL, 1 N in tetrahydrofuran) at 0° C. 3,5-Dichloro-4-(4-nitrophenoxy)trimetylsilylacetylenebenzene (26 g) in tetrahydrofuran (400 mL) was added dropwise at 0° C. and the reaction mixture was stirred at this temperature for two hours. A mixture of sodium hydroxide (170 mL, 1 N) and methanol (200 mL) was added dropwise at 0° C. followed by dropwise addition of hydrogenperoxide (90 mL, 27% w/w) at the same temperature; The mixture was stirred at 0° C. for an additional hour and concentrated. The remaining aqueous solution was acidified with hydrochloric acid (1.2 N) and extracted with three times ethyl acetate. Concentration of the organic phase gave a dark oil which was used in the next step without further purification.

(e) The crude product above was dissolved in methanol (300 mL) and thionyl chloride (8.1 g) was carefully added. The mixture was stirred at reflux for two hours. The reaction mixture was concentrated, water was added and extracted three times with ethyl acetate. Purification on column (silica, n-heptane/ethyl acetate, 4:1) gave 15 g of methyl[3,5-dichloro-4-(4-nitrophenoxy)phenyl]acetate.

(f) To a solution of methyl[3,5-dichloro-4-(4-nitrophenoxy)phenyl-3 acetate (14 g) in ethyl acetate (90 mL) was added platinum (IV) oxide monohydrate (0.48 g) and the mixture was stirred vigorously under hydrogen gas (1 atmospheres) for 6 hours. The suspension was filtered and the filtrate concentrated. The residue was purified on column (silica gel, n-heptane/ethyl acetate, 1:1) to give 7.0 g of methyl[3,5-dichloro-4-(4-aminophenoxy)-phenyl]acetate as orange crystals.

(g) A stirred mixture consisting of methyl[3,5-dichloro-4-(4-aminophenoxy)phenyl]acetate (0.32 g), benzaldehyde (0.20 g), sodium cyanoborohydride (0.03 g), methanol (15 mL) and one drop of acetic acid was stirred at room temperature for 5 days. The reaction mixture was concentrated and the residue partionated between ethyl acetate and sodium hydrogen-carbonate (saturated aqueous solution). The aqueous phase was further extracted with ethyl acetate. The collected organic phases were purified on column (silica gel, n-heptane/ethyl acetate, 9:1) to give 0.36 g of methyl [3,5-dichloro-4-(4-benzylaminophenoxy)phenyl]acetate.

(h) To a stirred mixture of methyl[3,5-dichloro-4-(4-benzylaminophenoxy)phenyl]acetate (0.36 g), triethylamine (0.10 g) and dichloromethane (40 mL) was added isobutyryl chloride (0.15 g). After 16 hours at room temperature, the reaction mixture was concentrated, and the residue partioned between ethyl acetate and water. The organic phase was washed with hydrochloric acid (1 N), a saturated aqueous solution of sodium hydrogencarbonate and brine. After concentration, the residue was purified on column (silica gel, petrolium ether/ethyl acetate, 4:1) to give, to give 0.40 g of methyl[3,5-dichloro-4-(4-(2-methylpropanoyl-benzylamino)phenoxy)phenyl]acetate.

(i) To a stirred solution of methyl[3,5-dichloro-4-(4-(2-methylpropanoylbenzyl-amino)phenoxy)phenyl) acetate in acetic acid (3 mL) was added one molar equivalent of nitric acid (70%) at 0° C. After two hours, ice and water was added, the aqueous phase extracted with ethyl acetate and concentrated. The residue was purified on column (silica gel, petrolium ether/ethyl acetate, 4:1) to give 0.44 g of methyl [3,5-dichloro-4-(3-nitro-4-(2-methylpropanoylbenzylamino)phenoxy)phenyl]acetate.

(j) Methyl[3,5-dichloro-4-(3-nitro-4-(2-methylpropanoyl-benzylamino)phenoxy)-phenyl]acetate (0.44 g), tin(II) chloride dihydrate and a mixture of ethyl acetate and ethanol (30 mL, 1:1) was heated at reflux for two hours. The reaction mixture was concentrated and the residue partionated between ethyl acetate and sodium hydroxide (1 N). The aqueous phase was further extracted with ethyl acetate. The collected organic phases were purified on column (silica gel, n-heptane/ethyl acetate, 4:1) to give 0.10 g of methyl [3,5-dibromo-4-(1-benzyl-2-isopropyl-5-benzoimidazolyloxy)phenyl]acetate.

(k) To a solution of methyl [3,5-dibromo-4-(1-benzyl-2-isopropyl-5-benzoimidazolyl-oxy)phenyl]acetate (100 mg) in ethyl acetate (20 mL) was added platinum (IV) oxide mono-hydrate (15 mg) and the mixture was stirred under hydrogen gas (1 atmospheres) for three days. The suspension was filtered and the filtrate concentrated. The residue was purified on column (silica gel, n-heptane/ethyl acetate, 1:1) to give 7.0 g of methyl ([3,5-dibromo-4-(2-isopropyl-5-benzoimidazolyloxy)phenyl]acetate. LC-MS: (M+1) m/z 393, (M−1) m/z 391.

(l) Methyl[3,5-dibromo-4-(2-isopropyl-5-benzoimidazolyloxy)phenyl]acetate (80 mg) was diluted in ethanol (15 mL) and treated with sodium hydroxide (1.0 mL, 1 N). The reaction mixture was stirred at room temperature for 16 hours. The reaction mixture was concentrated, the residue partioned between ethylacetate and hydrochloric acid (1 N). The organic phase was concentrated and further purified on column (silica gel, chloroform/methanol/acetic acid, 90:10:1) to give 60 mg of 3,5-dichloro-4-(2-isopropyl-5-benzimidazol-yloxy)phenylacetic acid. $^1$H-NMR (270 MHz, methanol-d$_4$): δ 1.41 (d, 6H), 3.22 (m, 1H), 3.70 (s, 2H), 6.82 (d, 1H), 6.88 (dd, 1H), 7.44 (s, 2H), 7.47 (d, 1H). 12.5 (br s, 1H), 7.86 (d, J=7.2 Hz, 2H), 7.34 (s, 2H), 7.61 (d, J=8.4 Hz, 1H), 7.50 (t, J=5.1 Hz, 3H), 7.42 (d, J=7.1, 1H), 7.35 (s, 1H), 6.87 (s, 1H), 3.70 (s, 2H).

Hangeland, Jon; Zhang, Minsheng; Caringal, Yolanda; Ryono, Denis; Li, Yi-lin; Malm, Johan; Liu, Ye; Garg, Neeraj; Litten, Chris; Garcia Collazo, Ana Maria; Koehler, Konrad; (Karo Bio A B, Swed.; et al.): Preparation of 4-(4-hydroxyphenoxy)phenyl-acetyl amino acids and related compounds as novel thyroid receptor ligands. *PCT Int. Appl.*, 60 pp. Application: WO 99-IB2084 19991223. Priority: GB 98-28442 19981224.

Example 6

3-{3,5-Dibromo-4-[2-(3-tolyl-5-benzofuranyloxy]phenyl}propionic Acid (a) To a suspension of bis(4-methoxyphenyl)iodonium tetrafluoroborate (3.3 g) (prepared analogously to the method of Yokayama et al, Journal of Medicinal Chemistry 1995, 38, 695–707) and copper bronze (0.56 g) in dichloromethane (10 mL), was added a solution of methyl(3,5-dibromo-4-hydroxyphenyl)propionate (1.50 g) (prepared according to: Li, Yi-Lin; Liu, Ye; Hedfors, Asa; Malm, Johan; Mellin, Charlotta; Zhang, Minsheng; (Karo Bio A B, Swed.; et al.): Preparation of 4-(4-hydroxyphenoxy)phenylacetic acid derivatives as novel thyroid receptor ligands. *PCT Int. Appl.*, 46 pp. Application: WO 98-EP4039 980626. Priority: GB 97-13739 970627) and triethylamine (0.7 mL g) in dichloromethane (6.5 mL) dropwise at room temperature. The mixture was stirred overnight and then filtered through a pad of silica gel. After concentration, the resulting residue was separated on a silica gel column eluted with ethyl acetate/light petroleum ether (2/8). The pure fractions were pooled and concentrated to dryness. The residue afforded 0.71 g of methyl [3,5-dibromo-4-(4-methoxyphenoxy)phenyl]propionate.

(b) methyl(3,5-dibromo-4-(4-methoxyphenoxy)phenyl] propionate (0.71 g), silver(I) sulfate (1.11 g) and methanol (50 mL) was stirred in the dark at −78° C. Iodide (0.83 g) was added and the reaction mixture was allowed to reach room temperature after 60 minutes. The yellow precipitate was filtered off, the eluate dissolved in ethyl actetate and washed with water. After concentration of the organic phase, the residue was purified on column (n-heptane/ethyl acetate 8:2) to give 0.54 g of methyl[3,5-dibromo-4-(4-methoxy-3-iodo-phenoxy)phenyl]propionate.

(c) Methyl[3,5-dibromo-4-(4-methoxy-3-iodophenoxy)phenyl]propionate (0.54 g) was dissolved in dichloromethane (4.2 mL) and boron trifluoride-methyl sulfide complex (4.2 mL) added at room temperature. The reaction mixture was stirred for 16 hours, water was added and the aqueous phase extracted with dichloromethane. The collected organic phases were concentrated in vacuo and separated on a column (silica gel, n cooled down to −78° C. Boron tribromide (8.8 mL, 1 N in dichloromethane) was added and the reaction mixture was stirred at −20° C. for 30 hours. Water was added to the reaction mixture, the organic phase separated and concentrated. The residue was was purified on column (n-heptane/ethyl acetate 8:2) to give 65 mg of methyl[3,5-dibromo-4-(4-hydroxy-3-iodophenoxy)phenyl]propionate as a beige solid mass.

(d) Methyl[3,5-dibromo-4-(4-hydroxy-3-iodophenoxy)phenyl]propionate (17 mg), 3-tolylacetylene (20 mg) and bis(triphenylphosphine)palladium(II) chloride (2.0 mg), copper(I) iodide (1.0 mg) and triethylamine (1 mL) was stirred at reflux. After 2 hours, the reaction mixture was cooled down, dichloromethane was added and washed once with a saturated solution of aqueous ammonium chloride. The organic phase concentrated and the residue purified on column (silica gel, n-heptane/ethyl acetate 8:2), to give 19 mg of methyl {3,5-dibromo-4-[2-(3-tolyl)-5-benzofuranyloxy]phenyl}propionate as a pale yellow solid mass. $^1$H-NMR (270 MHz, Acetone-$d_6$): δ 7.68 (s, 2H), 7.53 (dd, 1H), 7.36 (t, 2H), 7.21 (d, 2H), 6.89 (m, 2H), 3.64 (s, 3H), 2.98 (t, 2H), 2.74 (t, 2H), 2.40 (s, 3H).

(e) Methyl{3,5-dibromo-4-[2-(3-tolyl)5-benzofuranyloxy]phenyl} propionate (19 mg) was dissolved in methanol (1 mL) and treated with sodium hydroxide (0.5 mL, 2 N). The reaction mixture was stirred at room temperature for 2.5 hours. The reaction mixture was treated with aqueous solution of hydrochloric acid (1 N), extracted with ethylacetate and concentrated. This gave 9 mg of 3-{3,5-dibromo-4-[2-(3-tolyl)-5-benzofuranyloxy]phenyl}propionic acid as a beige solid mass.

The invention claimed is:

1. A compound of the general formula:

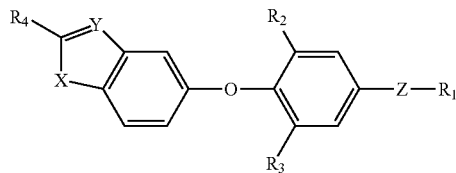

or pharmaceutically acceptable salts, stereoisomers, prodrug ester forms or radioactive forms thereof, wherein;
$R_1$ is selected from: carboxylic acid (—$CO_2H$), phosphonic acid (—$PO(OH)_2$), phosphamic acid (—$PO(OH)NH_2$), sulphonic acid (—$SO_2OH$), and hydroxamic acid (—CONHOH) groups;
Z is selected from: —$(CH_2)_n$—, and —$(CH_2)_mCH(R^a)$—;
$R_2$ and $R_3$ are independently selected from: halogen, $C_{1-4}$ alkyl, and $C_{1-4}$ alkyl substituted with 1, 2 or 3 $R^b$ groups which may be the same or different;
$R_4$ is selected from: $C_{6-10}$ aryl, $C_{5-9}$ heteroaryl, $C_{1-4}$ alkyl, and $C_{1-4}$ alkyl substituted with 1, 2, or 3 $R^c$ groups which may be the same or different, said aryl and heteroaryl being optionally substituted with 1, 2, or 3 $R^d$ groups which may be the same or different;
X is selected from: —O—, —S—, and —$N(R^e)$—;
Y is selected from: —CH—, and —N—;
$R^a$ is selected from: —OH, —$NH_2$, —$NH(C_{1-4}alkyl)$, —$NH(C_{2-4}alkenyl)$, and —$NH(C_{2-4}alkynyl)$, or a bioisosteric equivalent;
$R^c$ is selected from: hydrogen, $C_{6-10}$ aryl, $C_{5-9}$ heteroaryl, $C_{6-10}$ aryloxy, $C_{5-9}$ heteroaryloxy, $N(C_{6-10}$ aryl)$_2$, —NH($C_{6-10}$ aryl), —$N(C_{5-9}$ heteroaryl)$_2$, —$NH(C_{6-9}$ heteroaryl), —$N(C_{1-4}$ alkyl)($C_{6-10}$ aryl), —$N(C_{1-4}$alkyl)($C_{6-9}$ heteroaryl), and —$N(C_{6-10}$ aryl)($C_{5-9}$ heteroaryl) or a bioisosteric equivalent;
$R^d$ is selected from: hydrogen, fluorine, —OH, $C_{1-2}$ alkoxy, $N(C_{1-4}$ alkyl)$_2$, and —$NH(C_{1-4}$ alkyl) or a bioisosteric equivalent;
$R^e$ is selected from: hydrogen, and $C_{1-2}$ alkyl;
n is 1, 2 or 3;
m 1 or 2.

2. A compound according to claim 1 wherein $R_1$ is a carboxylic acid (—$CO_2H$).

3. A compound according to claim 1 wherein $R_2$ and $R_3$ are bromine.

4. A compound according to claim 1 wherein $R_2$ and $R_3$ are chlorine.

5. A compound according to claim 1, wherein n is 1 or 2, m is 1, and $R^a$ is —OH or —$NH_2$.

6. A compound according to claim 1, wherein $R^c$ and $R^d$ are hydrogen.

7. A compound according to claim 1, wherein X is —O—, and Y is —CH—.

8. A compound according to claim 1, wherein X is —$N(R^e)$—, and Y is —N— or —CH—.

9. A compound according to claim 1 wherein Z is —$(CH_2)_n$—, $R_2$ and $R_3$ are independently chlorine or bromine, $R_4$ is $C_{1-4}$ alkyl, X is —N($R^e$)—, Y is —N—, $R^c$ is hydrogen, $R^e$ is hydrogen or $C_{1-2}$ alkyl, and n is 1.

10. A compound according to claim 1 wherein $R_2$ and $R_3$ is bromine, X is —O—, Y is —CH— $R^a$ is —OH or H, $R^c$ is $C_{6-10}$ aryl or $C_{6-10}$ aryloxy, $R^d$ is hydrogen or $C_{1-4}$ alkyl, n is 1 or 2; and m is 1.

11. A compound according to claim 10 wherein $R_4$ is $C_{6-10}$ aryl or $C_{5-9}$ heteroaryl; Z is —(CH$_2$)$_n$—; and $R^d$ is hydrogen.

12. A compound selected from:
    3,5-Dibromo-4-(2-phenyl-5-benzofuranyloxy) phenylacetic acid;
    3,5-Dibromo-4-(5-benzimidazolyloxy)phenylacetic acid;
    3,5-Dibromo-4-(1-N-methyl-5-benzoimidazolyloxy) phenylacetic acid;
    3,5-Dibromo-4-(2-methyl-5-benzimidazolyloxy) phenylacetic acid;
    3,5-Dichloro-4-(2-isopropyl-5-benzimidazolyloxy) phenylacetic acid;
    3-{3,5-Dibromo-4-[2-(3-tolyl)-5-benzofuranyloxy] phenyl}propionic acid;
    and pharmaceutically acceptable salts thereof, and stereoisomers thereof.

13. A compound according to claim 1, which has one or more asymmetric centers and can exist in the form of a racemate, a single or multiple enantiomer, an individual diastereomer thereof.

14. A pharmaceutical composition comprising an effective amount of a compound according to claim 1, or a pharmaceutically effective salt thereof, together with a pharmaceutically acceptable carrier.

* * * * *